(12) United States Patent
Prentice et al.

(10) Patent No.: US 7,575,676 B2
(45) Date of Patent: Aug. 18, 2009

(54) HPLC COLUMN HOLDER APPARATUS

(75) Inventors: David P. Prentice, Millville, MA (US);
Roger Gilman, Mendon, MA (US);
Brett G. Cook, Middleboro, MA (US)

(73) Assignee: Waters Technologies Corporation,
Milford, MA (US)

( * ) Notice: Subject to any disclaimer, the term of this patent is extended or adjusted under 35 U.S.C. 154(b) by 330 days.

(21) Appl. No.: 10/963,276

(22) Filed: Oct. 12, 2004

(65) Prior Publication Data

US 2006/0008390 A1    Jan. 12, 2006

(51) Int. Cl.
*F16M 11/00*    (2006.01)
*B01L 9/00*    (2006.01)
*B01D 15/00*    (2006.01)

(52) U.S. Cl. .................... 210/198.2; 210/636; 210/656; 73/23.39; 73/23.36; 73/61.52; 73/61.53; 422/104; 96/101; 96/106; 96/104; 248/188; 248/200.1; 248/519

(58) Field of Classification Search ....................... None
See application file for complete search history.

(56) References Cited

U.S. PATENT DOCUMENTS

| 2,516,965 | A | * | 8/1950 | Dresser ..................... 211/60.1 |
| 2,904,408 | A | * | 9/1959 | Gill ............................ 422/104 |
| 3,640,813 | A | | 2/1972 | Nerenberg |
| 4,451,365 | A | | 5/1984 | Sattler |
| 4,732,672 | A | | 3/1988 | Kiang |
| 5,023,755 | A | | 6/1991 | Rosenberg |
| 5,772,625 | A | * | 6/1998 | Krueger et al. ................. 604/9 |
| 5,979,846 | A | * | 11/1999 | Fluhr ......................... 248/200 |
| 6,352,076 | B1 | * | 3/2002 | French .................. 128/203.12 |

FOREIGN PATENT DOCUMENTS

JP    62-42052    2/1987

* cited by examiner

*Primary Examiner*—Krishnan S Menon
(74) *Attorney, Agent, or Firm*—Anthony J. Janiuk

(57) ABSTRACT

An HPLC column holding apparatus used to mount an HPLC column in one of a plurality of positions is disclosed herein. The apparatus comprises a clip-device interface that secures the apparatus to a platform and a clip-column interface that secures the HPLC column to the apparatus.

15 Claims, 13 Drawing Sheets

HPLC COLUMN HOLDER APPARATUS

STATEMENT ON FEDERALLY SPONSORED RESEARCH

N/A

FIELD OF INVENTION

This invention pertains to an apparatus used to mount one or more high performance liquid chromatography columns.

BACKGROUND OF THE INVENTION

High Performance Liquid Chromatography (hereinafter "HPLC) allows for fast and efficient separation and characterization of analytes within a given sample. Components of an HPLC system include high pressure pumps which facilitate the movement of an aqueous phase through the system. This aqueous phase (or mobile phase) comprises a solvent that is used to initially equilibrate the HPLC system. The solvent also provides an aqueous milieu for analytes to traverse through the entire HPLC system. Finally, the mobile phase comprises solvent which elutes analytes from an HPLC column.

Another component of an HPLC system is the chromatography separations column. The column comprises a solid phase. The solid phase, in combination with the mobile phase, effectuates differential separation of analytes contained within a sample matrix. The solid phase generally consists of chemical polymers that interact with a certain class of analyes. For example, ion-exchange HPLC columns have a solid phase chemistry that interacts specifically with analytes that are ions. To illustrate this principle, anion-exchange columns have a solid phase cationic functional group that will interact, in a non-covalent manner, with anions present in the sample matrix. Depending upon the mobile phase conditions passing through the column, certain anions of the sample will be eluted from the column's solid phase, while other anions of the sample will be retained.

Once the analytes are eluted from the column, they traverse into and through a detector. There are a variety of detection systems that can be employed in an HPLC system. For example, there are ultra-violet ("UV") detectors that detect analytes within the UV range.

The fluidics of any HPLC system requires the presence of tubing that serve as passageways for the mobile phase throughout the entire system. Separation columns are in fluidic connection with the mobile phase via this tubing. The tubing connects the column to the fluidics via HPLC fittings (or simply "fitting"). An HPLC fitting is a tubular structure having a first end with a circumferential design with an orifice that allows for entry and penetration by the fluidics tubing. The fitting also comprises a second end that is generally conically shaped. The second end of the fitting also comprises an orifice that allows for the mobile phase to exit the fitting and enter a column through its connection to the fiting. The fiting has a hollow channel through which the mobile phase can traverse through the fining. The exterior surface of the fitting is threaded such that it can be screwed securely into proper position within an end of the HPLC column. Given that HPLC columns have two threaded ends, there are typically two threaded fittings used to facilitate the fluidic connection of a column to the rest of the HPLC system.

An issue that plaques practitioners of chromatography is how to mount and/or secure a column while in use or otherwise. Some HPLC systems have a heating/cooling component that secures a column within the unit, however, access to the column in these particular systems is limited and difficult for the practitioner. There clearly exists a need for an HPLC column mount that can hold one of more columns that are easily accessible to a practitioner.

SUMMARY OF THE INVENTION

The present invention pertains to a column holding apparatus, referred to as a clip, used to secure an HPLC column in one of a plurality of positions disposed along a securing means device. The clip comprises a clip-device interface and a clip-column interface.

The clip-device interface (or simply "device-interface") is a portion of a clip that interacts with a securing means device, such as a bar, wire, or alike. The function of the device-interface is to facilitate affixing the securing device to the clip. The device-interface can have any configuration provided that it facilitates interaction with the securing device. In one aspect of the present invention, the device-interface has a square-like geometrical configuration that defines a square-like orifice in which a device having a square-like superficial surface, such as a square bar, is disposed within this orifice in a manner sufficient to secure the clip. Other geometerical configurations of the device-interface are envisaged to be within the scope of this invention. For example, the securing device can be a thin, flat bar that can be maneuvered into position about a clip. In this instance, the clip can comprise one or more side elements used to guide and secure a fit between the clip and device. Other examples of securing devices include, but are not limited to, chromatography hardware (e.g., pumps, etc.), strings, wires, and alike.

The securing devices of the instant invention can be used to affix one or more clips to an apparatus. For example, a wire can be disposed from an apparatus using one end of the wire while a second end of the wire is affixed to the clip, thereby affixing the clip to the apparatus. In one particular embodiment of the present invention, the securing device is a bar that secures the clip to a base element facilitating the entire apparatus (i.e., the clip, column, and securing device) to rest upon a surface such as atop a laboratory bench.

The device-interface can also comprise one or more elements that facilitate direct attachment of a clip to an apparatus. A clip can be affixed to a securing device independent of a securing device. In one embodiment, a clip facilitates positioning of an HPLC column about an apparatus such as a chromatographic machine using components that grasp onto the apparatus. In this embodiment, the clip comprises elements, for example, protruding leg elements, that interact with the apparatus thus allowing the clip and column to be affixed to the apparatus. The clip's components can also comprise a suction-cup device that can be used to secure the attachment of a clip onto the surface of an apparatus. Other means of attaching a clip to an apparatus are envisaged to be within the scope of this invention. For example, velcro can be used to affix a clip onto the surface of an apparatus.

The clip-column interface (or simply "column-interface) component is a portion of the clip that interacts with and secures an HPLC column. The column-interface can have various configurations, its only requirement is that it must be suitable in securing an HPLC column to the clip. For example, it can have a fork-like construction with an orifice being defined within the column-interface. In this particular embodiment, the fork-like construction is formed by a crevice defined by the column interface. This fork-like component is pliable enough to permit the column-interface to transition from a first (or relaxed) position to a second (or strained)

position thus allowing the column interface to engage an HPLC fitting. Once the fitting has been disposed about the orifice, the column-interface can re-assume the first or relaxed position. Other embodiments include a column-interface having a solid, fully integrated surface that defines an orifice capable of accepting an HPLC fining. The function of the column-interface is to facilitate affixing an HPLC column to the clip.

DETAILED DESCRIPTION

The present invention pertains to a column holding apparatus (a "clip") 10 used to secure an HPLC column 20 in one of a plurality of positions disposed along a securing means, such as a bar 16. See FIGS. 1-13. The clip 10 comprises a clip-device interface ("device-interface") 12 and at least one clip-column interface ("column-interface") 14. (in order to simplify the discussion that follows, only one clip will be discussed viz. the securing of an HPLC column. However, it should be understood that typically at least two clips are used to secure one HPLC column. Therefore, the discussion of one clip applies to a plurality of clips, unless clearly stated to the contrary.)

The clip 10 of the present invention can be disposed on a securing means device (or simply "device"), such as a bar 16. See FIGS. 9, 10 and 13. The securing device can hold one or more clips 10. Further, the clips disposed along a securing device need not be in parallel, they can be disposed askewed to one another. Obviously, if two clips are being employed per column, then the pair will be disposed in parallel to one another, however, other pairs of clips (securing other columns) can be disposed at different angles from each other.

Figure 1:
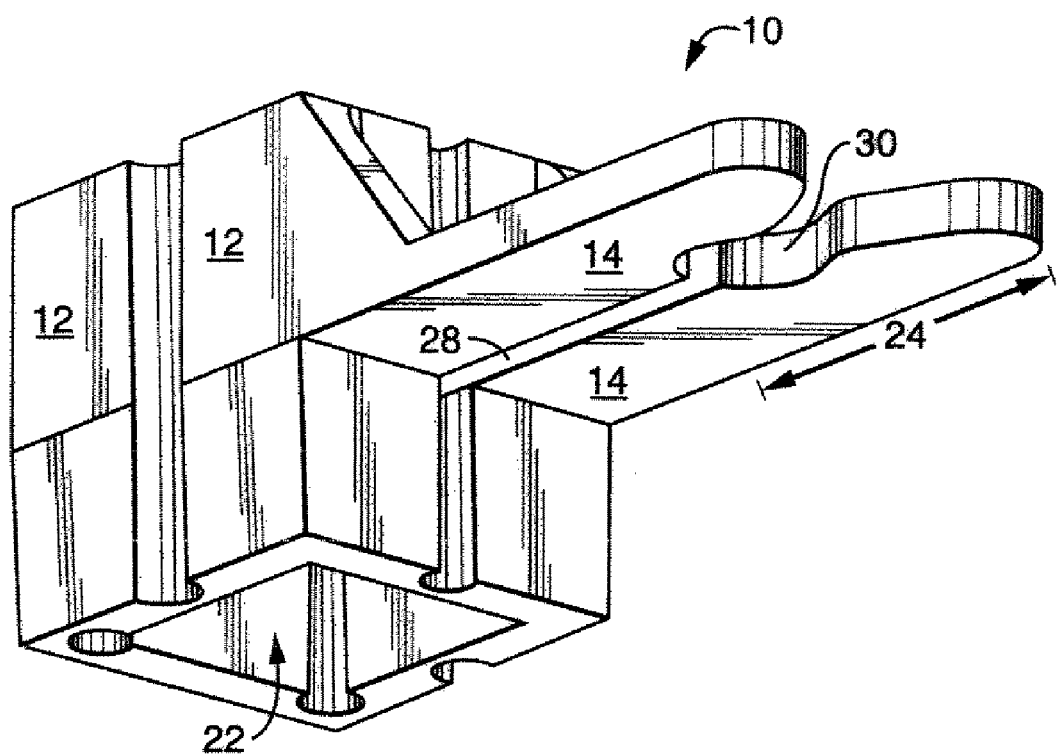
FIG. 1 is a schematic representation of a clip.
Figure 2:
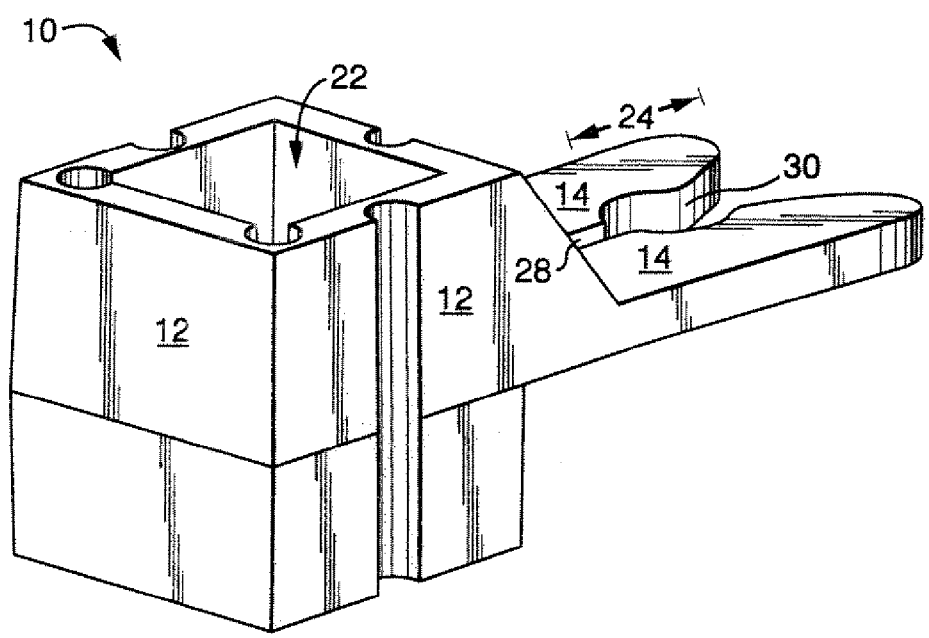
FIG. 2 is a schematic representation of the clip of FIG. 1 shown from a different perspective.
Figure 3A:
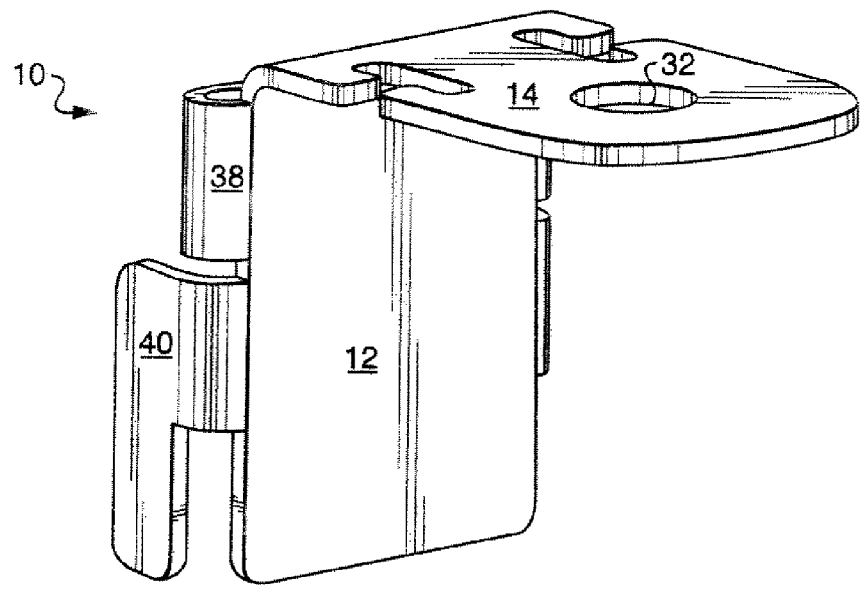
FIG. 3 (a) is a schematic representation of a clip; (b) is the same clip only viewed at a different orientation.
Figure 3B:
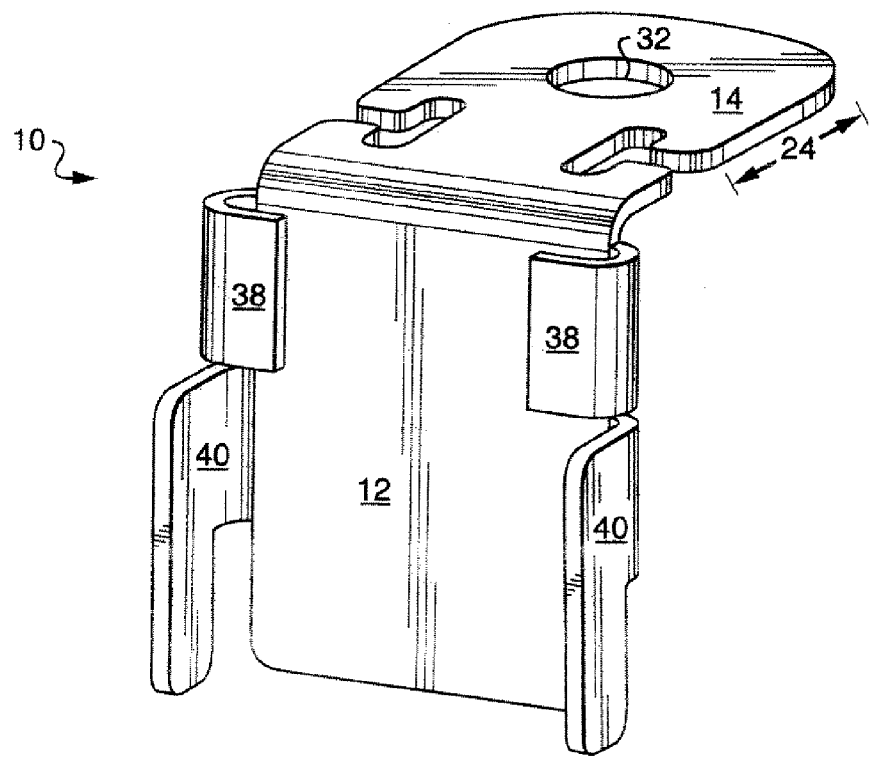

This invention facilitates the mounting of one or more HPLC columns 20 onto a device. The clip 10 can comprise elements designed to secure the clip 10 itself with or without a column affixed thereto, directly onto (or into) an apparatus. For example, FIG. 3 depicts protruding leg elements 40 that can be used to attach a clip or sliding feature onto an apparatus. Further, the clip can be disposed upon a base platform 18 that in turn can be at rest upon a surface such as a laboratory bench (see FIG. 13).

The clip-device interface 12 of the present invention can have any geometry. The only requirement for the device-interface 12 is that its geometry be sufficiently complimentary to a securing mean's (like a bar) geometry. For example, the device-interface 12 can have a square-like geometry wherein four walls (or three in the case of FIG. 6) of essentially equal dimension define an orifice 22 which is used to secure the device-interface 12 on a device (in this case a bar) 16 having a square-like superficial surface. See FIGS. 1-6 and 9-13. The dimensions of the device-interface 12 can vary depending upon, for example, the securing device and its dimensions. It is important that the dimensions of the device-interface 12 accommodate the dimensions of the securing device. For example, the securing device can be a bar having a square-like surface ranging in width from about 6.35 mm to about 19.05 mm (or greater). A device-interface that is disposed along this bar will necessarily define an orifice that can accommodate the dimensions of the securing device, in the present example a square bar. Once disposed onto (or into) a securing means device like a bar, the device-interface 12 can be positioned along the bar 16 at any desired location.

Figure 9:
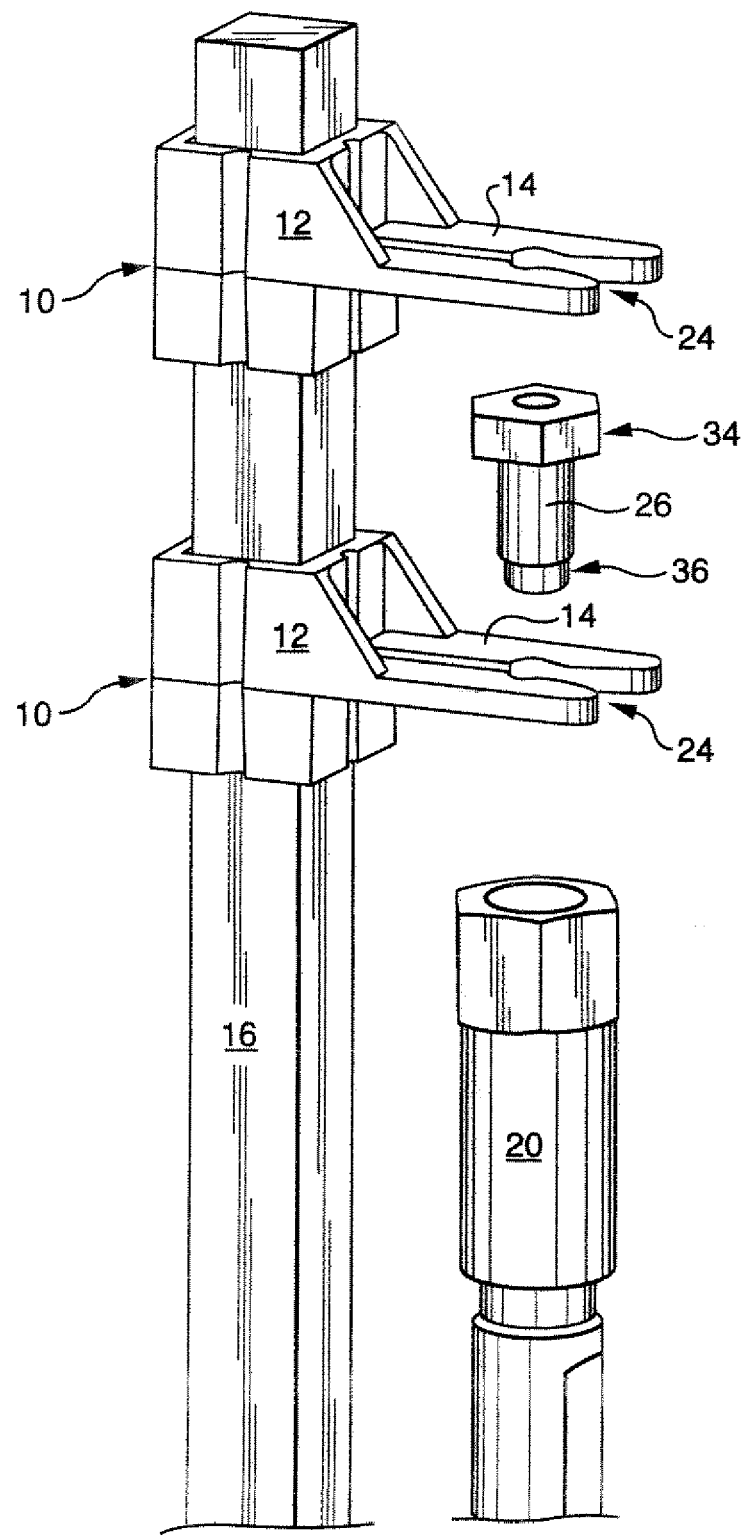
FIG. 9 is a schematic representation of a clip disposed along a bar together with a column prior to the column being secured.
Figure 10A:
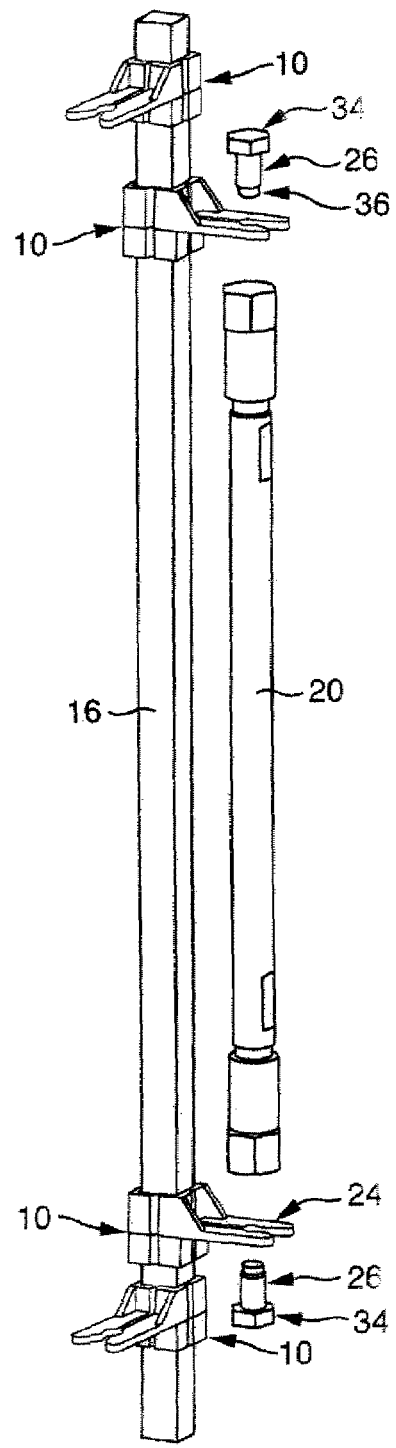
FIG. 10 (a) shows a column holding apparatus together with a column and its fittings prior to being secured by the apparatus; (b) shows a column securely affixed to a column holding apparatus.
Figure 10B:
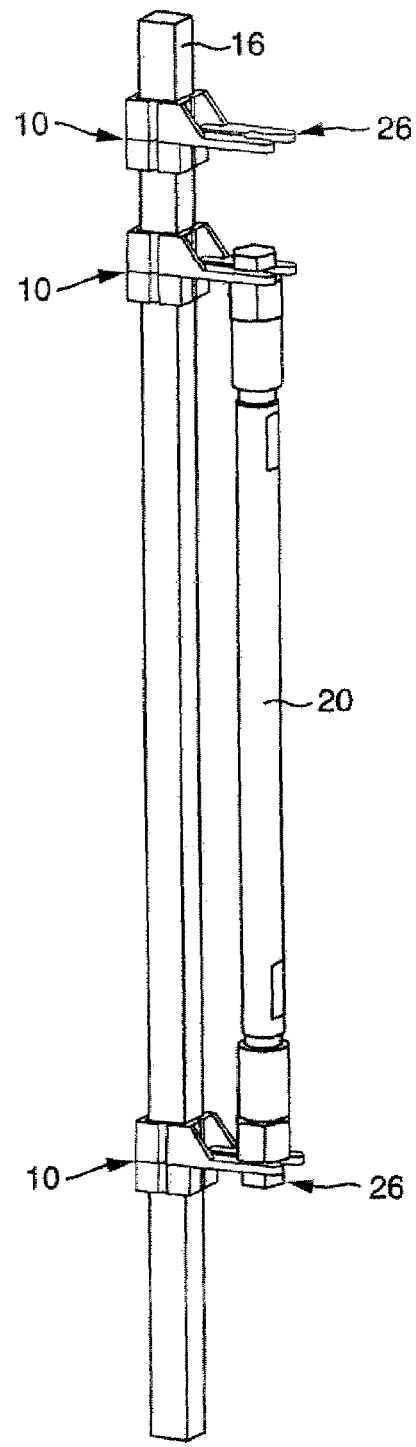
Figure 13:
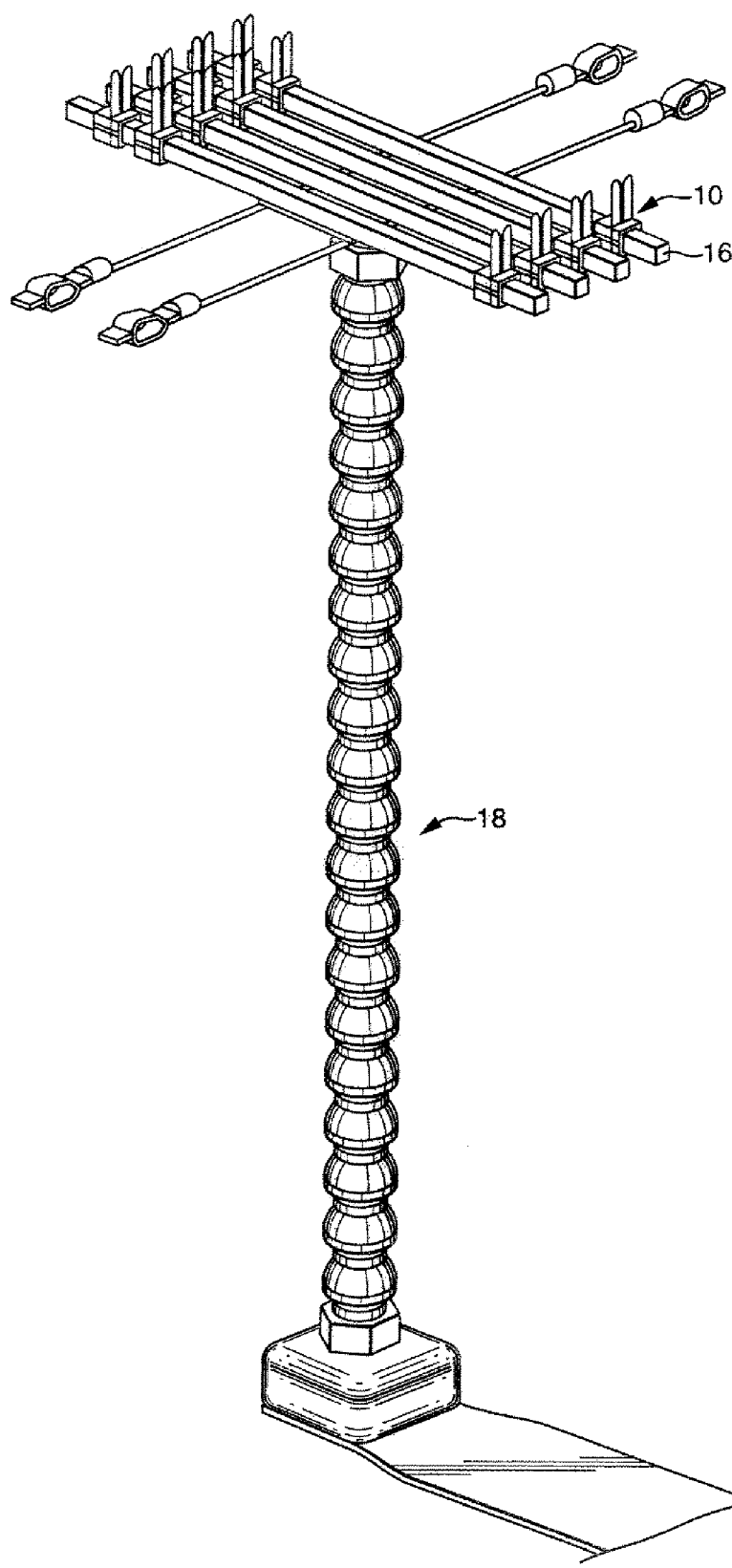
FIG. 13 shows one embodiment of the present invention having several clip devices being secured by a base stand.

The device-interface 12 can define a circular orifice that can be disposed on a securing device having a circular superficial surface (not shown). In this example, preferably the fit between the device-interface and bar is such that sufficient surface friction exists between the device-interface and bar so that rotation of the device-interface about the bar is minimized. If however, the bar has a polygonal surface, as illustrated in FIGS. 9, 10 and 13, and the orifice 22 defined by the device-interface 12 is complimentary to the bar's geometry, then a saw-tooth effect (most effective for polygonal surfaces $\geq 3$) will obviate rotation of the interface about the complimentary bar. A further example of a securing device is a thin, flat bar. The device-interface that can interact with this type of securing device can comprise side elements 38 as depicted in FIG. 3 into which this thin, flat securing bar can fit.

Securing devices other than bar-like objects are embraced by this invention. For example, a string or wire-like device can be threaded through, for example, an orifice defined within the device-interface thereby facilitating the attachment of a clip to some chromatographic machine or alike. It should be obvious to those skilled in the art that other means of securing a wire or string-like object to a clip can be employed other than using an orifice defined by the clip. For example, a hook-like projection formed on a surface of a clip can be used to secure string or wire. In one embodiment, a first end of the wire-like securing device is attached to an apparatus via any reasonable means known to those skilled in the art, while the second end is affixed to a clip, thereby affixing the clip to the apparatus. The first end need not be attached to an apparatus, rather it can be attached to office equipment/furniture, for example, a shelf or alike.

The device-interface can be securely disposed about an apparatus in any means reasonable known to those skilled in the art. In one embodiment of the present invention, a securing device having a longitudinal axis can comprise one or more channels bored into it along its longitudinal axis wherein only a device-interface having complimentary protruding elements can fit securing onto and along the device without the possibility of displacement (not shown). In this embodiment, the device-interface element can have less protruding elements than the number of channels bored into the device. However, to minimize rotation and longitudinal slippage of the device-interface about the securing device, at least one protruding element is preferably disposed on the device-interface.

There are other means for securing a device-interface to a device such as a bar 16. In one particular aspect of the present invention, the device-interface has one or more walls defining an orifice whereby a device can be disposed. In this particular embodiment at least one wall of the device-interface has a threaded orifice such that a suitable screw can be threaded through the threaded orifice in apposition to a surface of the device (not shown). By increasing the number of turns of the screw disposed adjacent to the surface of the device, until the screw resists any further turning, the device-interface 12 will be securely disposed adjacent to the device.

In another aspect, the securing device itself comprises a threaded orifice (not shown). A device-interface having an orifice can be disposed along the securing device in proper alignment such that the threaded orifices of the device-interface and securing device line up in apposition, then a suitable screw can be used to affix the device-interface to the device. In this particular aspect, the device-interface's orifice can be threaded or non-threaded.

In one embodiment, the device-interface and securing device each have an orifice which when properly aligned are in apposition. In his embodiment, the orifices need not be threaded. The clip can be secured into position in this embodiment via a holding pin that is placed through the device-interface orifice and the orifice of the securing device.

A particular aspect of the above-described embodiment is that the securing device comprises an orifice that extends entirely through the device having a first and second opening. In a particular aspect, a straight linear axis is defined by the first and second openings. The device-interface comprises an orifice defined by one wall of the device-interface and another orifice defined by a wall opposite the first wall. In this particular aspect, once the orifices of the device and device-interface are properly aligned, a hold pin (or screw and nut or alike) can be placed through the orifices in order to secure the securing device and device-interface (not shown).

Figure 4:
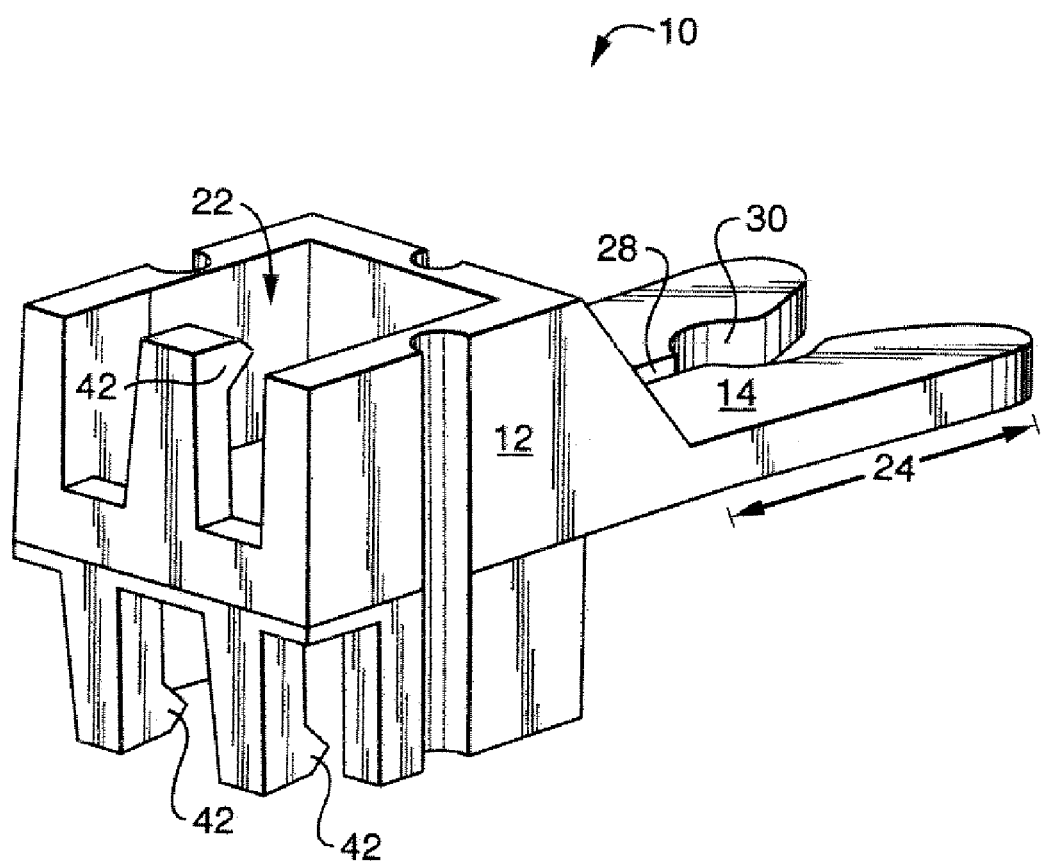
FIG. 4 is a schematic representation of one embodiment of the present invention.
Figure 7:
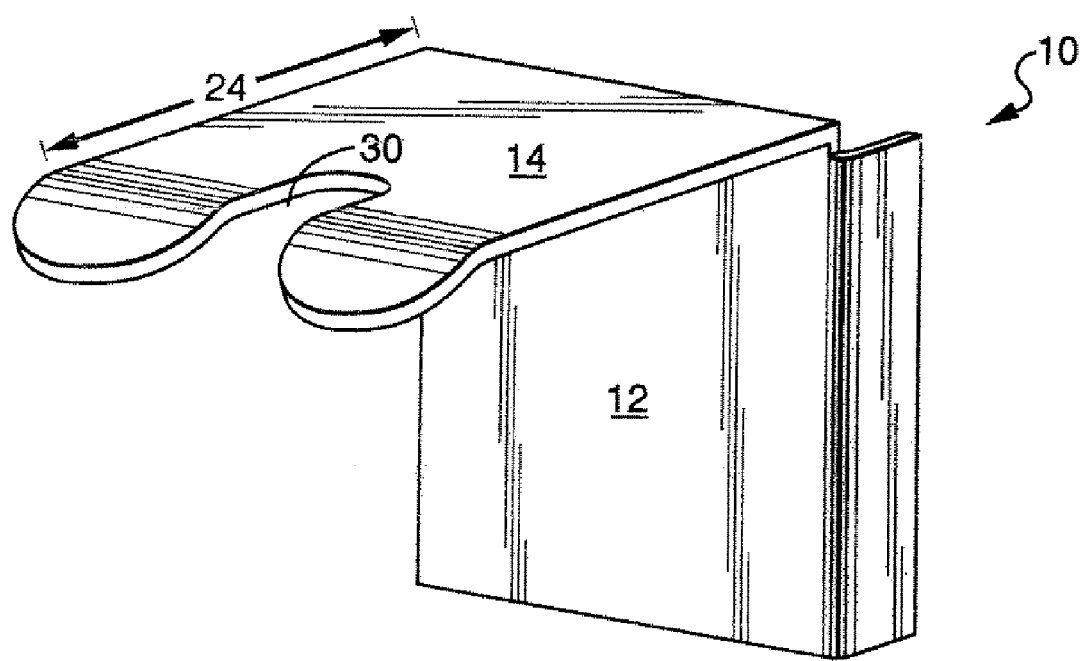
FIG. 7 is a schematic representation of one embodiment of the present invention.
Figure 8:
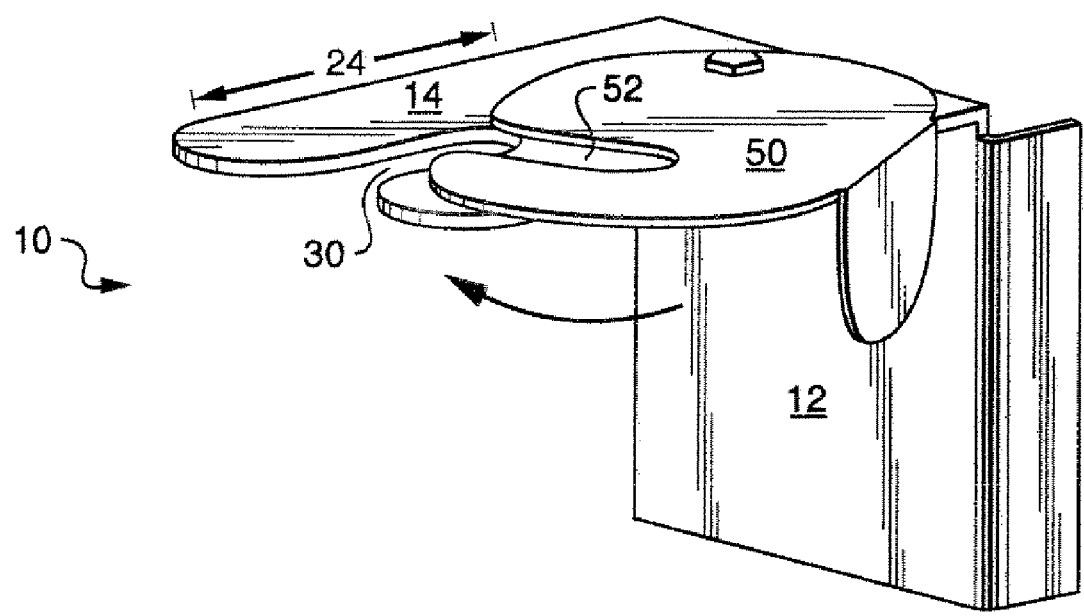
FIG. 8 is a schematic representation of one embodiment of the present invention.

Other means for securing a device-interface to a bar can be envisaged by one skilled in the art and is considered to be within the scope of the present invention. FIG. 4 illustrates a device-interface 12 having one or more tooth-like elements 42 that can interact with a securing device having at least one dentated track along its superficial surface. FIGS. 7 and 8 depict another embodiment employed for affixing a clip with a securing device. Additional means include, but are not limited to, a knurled bar having one or more spring pins including a bi-metal flat leaf spring.

Figure 5:
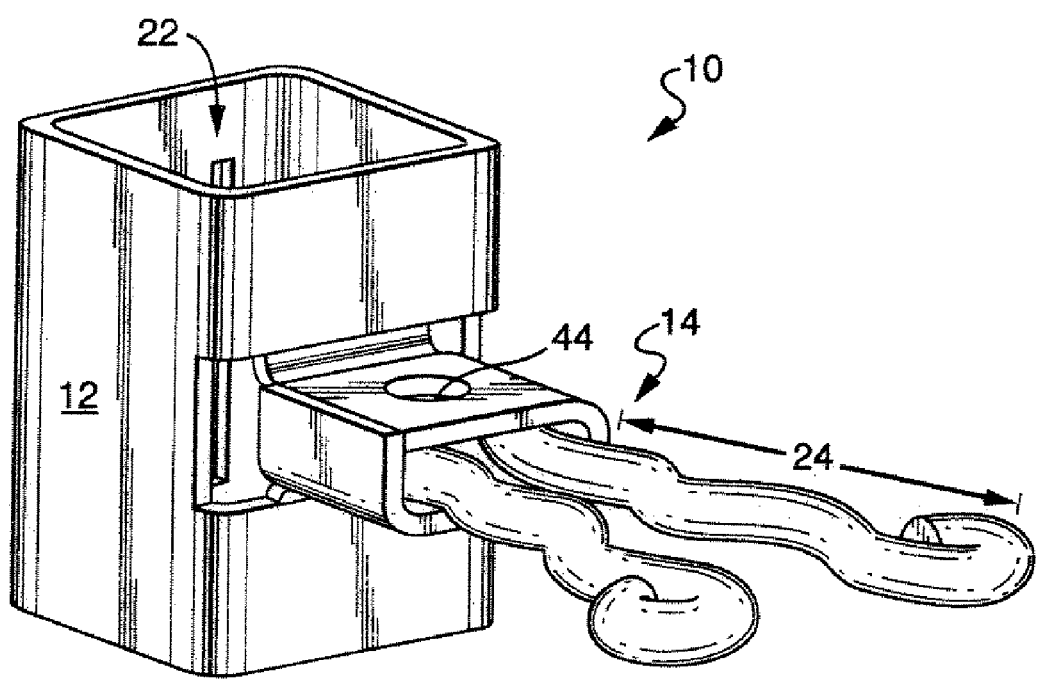
FIG. 5 is a schematic representation of one embodiment of the present invention.

The column holding apparatus 10 of the present invention comprises one or more clip-column interfaces 14. See FIGS. 1-13. These figures illustrate embodiments of the present invention wherein the column-interface 14 is structurally contiguous with the device-interface 12. In an alternative embodiment, the column-interface 14 is a separate structure independent from the device-interface 12 that can be securely affixed to the device-interface 12 by means well known to those skilled in the art (not shown). Also, the present invention contemplates, as depicted in FIG. 5, that the column-interface 14 can be interchangeably removable from the device-interface 12. It is conceivable that the orifice 44 depicted in FIG. 5 facilitates securing the column-interface 14 to the device-interface 12 using, for example, a suitable pin or screw disposed through the orifice 44 and column-interface 14. Typically the length of the column-interface 14 ranges from about 0.25 inches to about 2.0 inches (or greater). The distal end of the column-interface 14 (i.e., distal to the device-interface 12) defines an element of the column-interface 14 that interacts with an HPLC column 20 or more precisely, one of its components. See FIGS. 1-13. This interaction is facilitated by a column-interface component that secures an HPLC fitting 26 that is threaded into an HPLC column 20. This column-interface element is referred to throughout as the "fitting grasper" 24 (or simply "grasper"). The grasper 24 can occupy from about ninety percent (or greater) to about twenty-five percent (or less) of the length of the column-interface 14.

Currently, there are three universally recognized HPLC fittings used in practice today. There is the 10-32, ¼-28, and M6 fitting. For the English type threads, the first number is the diameter of the threaded portion of the fitting (not the tubing) and the second number gives the number of threads per inch. However, thread sizes smaller than ¼ inches are described by a number from 1-12, corresponding to diameters of 0.073-0.216 inches. A 10-32 thread is 0.190 inches in diameter and has 32 threads per inch. An M6 fitting has one thread per mm and a diameter of 6 mm. Male nuts with similar thread sizes cannot be interchanged if the length of the threads differ.

The grasper 24 of the present invention is capable of interacting with any of the fittings listed above. When a fitting is threaded into place on an HPLC column there exist a gap between the top 34 of the fitting 26 and the HPLC column 20. It is this gap portion of the fitting with which the grasper 24 interacts. See FIGS. 9-10. The distance of the gap can vary, but it typically ranges from about 0.060 inches or greater. In a particular aspect, the fitting is already securely threaded into the column. Alternatively, the fitting can be secured by the grasper 24 prior to the fining being threaded into the column. See FIG. 10.

The column-interface 14 comprising the grasper 24 can be of any configuration. In one embodiment, the grasper 24 forms a fork-like structure in which a mid-line crevice 28 extends from the distal end of the column-interface to a position proximal to the device-interface 12. See FIGS. 1, 2, 4, 11 and 12. In this embodiment, the crevice 28 has a circular enlargement 30 toward the distal end of the column-interface 14 having dimensions such that an HPLC column fitting 26 can be securely positioned within it. The diameter of the enlargement 30 is sufficient to accommodate HPLC fittings. In particular, a region distal from the top 34 of the fitting 26 is securely disposed within a grasper 24.

Different fittings can have various geometries such as a conical threaded region wherein the diameter changes and becomes narrower as the distal tip 36 of the fitting 26 is approached. Alternatively, the entire threaded region of a fining can be of the same diameter. The column-interface 14 of the present invention accommodates all variations of fittings. The precise location of the circular enlargement 30 along the column-interface 14 is not critical, however, it must be able to effectively secure a fitting 26 without interference from the device-interface 12. It is conceivable that if the enlargement is positioned too close to the device-interface 12, then a column 20 will not be secured to the clip 10 due to interference between a portion of the column 20 and the device-interface 12. In one particular aspect of this embodiment, the column-interface 14 is sufficiently pliable to permit the penetration of a fitting 26 (perhaps by a snap-fit mechanism) into a circular enlargement 30, but remain sufficiently strong enough to secure the fitting 26 once within the parameters of the circular enlargement 30. See FIG. 10.

In another embodiment, the grasper 24 defines an orifice 32 in which a fitting 26 can be placed through the orifice and threaded into one end of an HPLC column 20. See FIG. 3. In this embodiment, the grasper's orifice 32 can be threaded or non-threaded. The circumference of the grasper's orifice 32 has to be large enough to permit intercourse with a fitting 26. The circumference of the orifice 32 is sufficient to accommodate an HPLC fitting 26. The fitting 26 can first be placed through the grasper's orifice and then screwed into position within one end of an HPLC column 20.

FIG. 5 illustrates yet another embodiment in which the grasper 24 comprises a pincher-like element. The grasper 24 and column fining (not shown) interact in a snap-fit manner. The distal end of the grasper 24 initiates interaction with the fitting and as the grasper 24 proceeds to encompass the fitting, the grasper 24 transitions from a first relaxed position to a second strained position. Once the grasper 24 fully encompasses circumferentially the fitting, the grasper 24 returns to its original first relaxed position.

Figure 6:
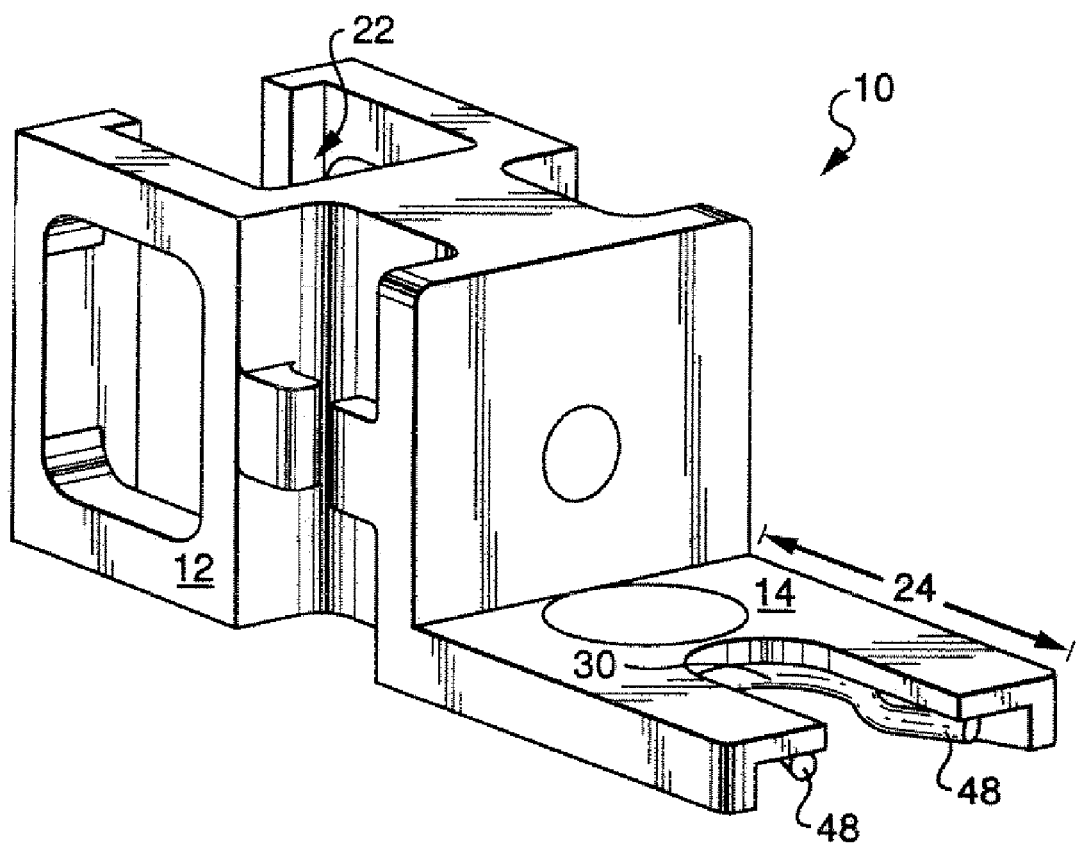
FIG. 6 is a schematic representation of one embodiment of the present invention.

FIG. 6 illustrates yet another embodiment of the present invention. In this embodiment, the grasper 24 comprises one or more lateral latches 48 that are displaceably moveable from a first position to a second position. In the first position, the latches 48 are disposed towards the interior of the orifice 30. As the grasper 24 interacts with an HPLC column fining (not shown) the latches 48 assume the second position. This second position is characterized by the latches 48 being recessed away from the interior of the orifice 30, thus permitting entry of the fitting into the orifice 30. Once the fining is disposed within the orifice 30, then the latches 48 assume the first position, thus securing the fining within the grasper 24. The displaceable movement of the latches 48 can be facilitated by a spring-like mechanism disposed between a lateral portion of the latches 48 and a lateral surface of the grasper 24. The precise mechanism can differ as one skilled in the art will appreciate.

FIG. 8 illustrates another embodiment of the present invention. In this embodiment, the grasper 24 defines an orifice 30 that can interact with an HPLC column fitting (not shown). To secure the fitting within the orifice 30, the grasper comprises a displaceably movable top latch 50 is position from a first, or open, position (as shown in FIG. 8) to a second, or locking, position (along the track defined by the arrow). The top latch 50 has a channel 52 that will receive the fitting as the top latch 50 assumes the second or locking position. Once the top latch 50 is in the second position, the fitting is secured within the confines of the grasper 24. In order to release the fitting, the top latch 50 is displaced from the second position to the first position.

Figure 11A:
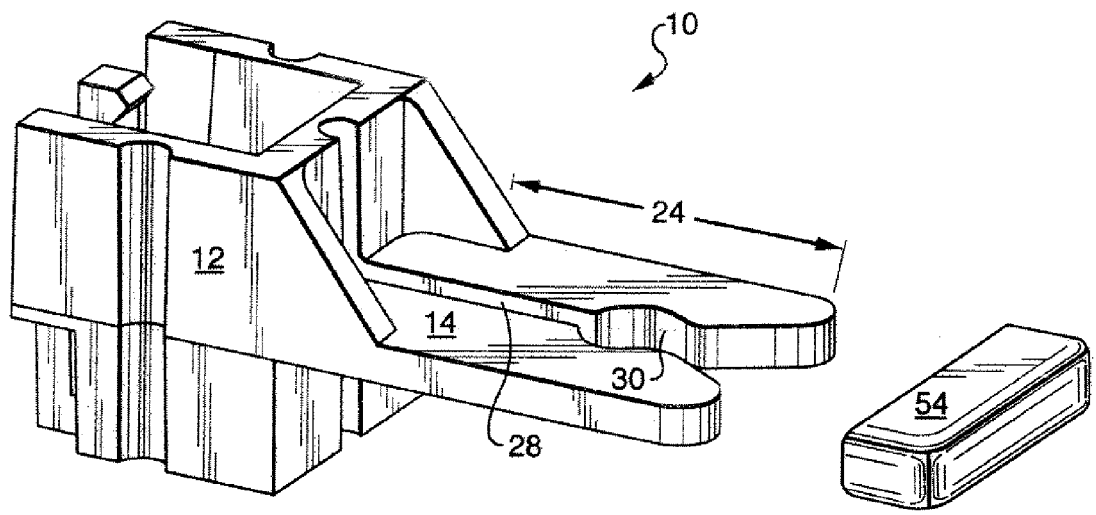
FIG. 11 (a) depicts a clip and a closure device; (b) depicts the closure device disposed upon the clip.
Figure 11B:
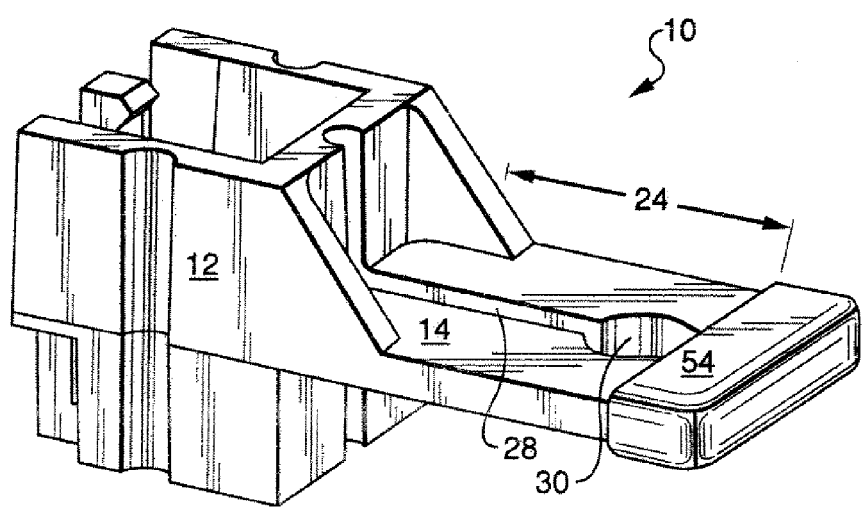
Figure 12A:
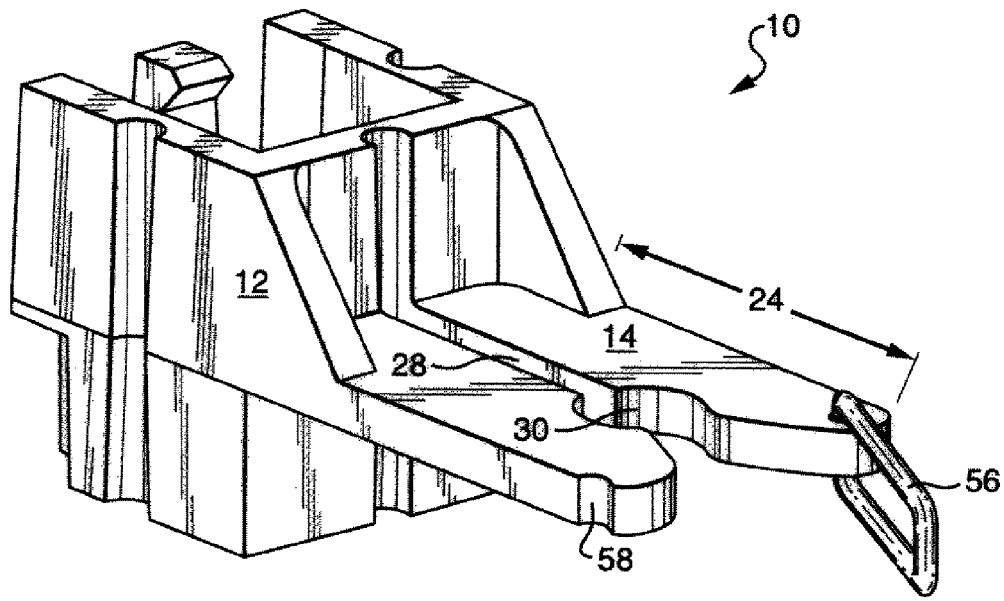
FIG. 12 (a) and (b) depicts another embodiment for a closure device.
Figure 12B:
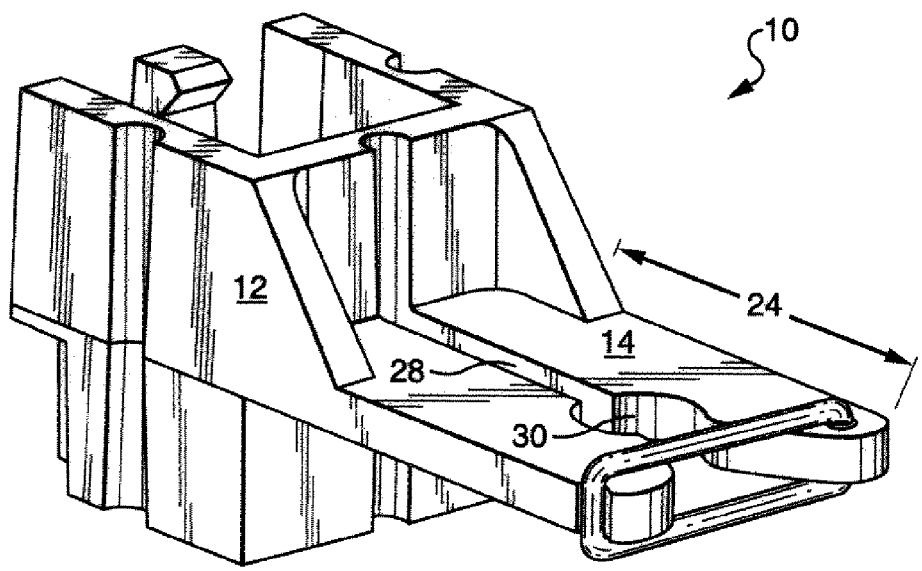

The present invention also includes embodiments wherein the grasper of a clip is securely closed. FIG. 11 (a) and (b) illustrates one embodiment used to effectuate closer of the grasper 24 thereby securing any item disposed therein. In this particular figure, a cap 54 is removably disposed onto the distal end of the grasper 24. The cap 54 can be securely affixed in any means reasonable known to those skilled in the art like a snap-fit mechanism. FIG. 12 (a) and (b) illustrates another embodiment for effectuating closer of the grasper 24. In this figure, a gate 56 is depicted wherein a first portion of the gate 56 is attached to a portion of the grasper 24. A second portion of the gate 56 is removably disposed onto the grasper 24 that has a cavity 58, thereby effectuating closure and securement of the grasper 24. Another aspect of this embodiment (not shown) comprises a grasper that has at least two cavities (similar to cavity 58) one on either fork component of the grasper. The gate, which is independent from the clip, can then be disposed onto the grasper and secured into position using the cavities that accept the gate.

FIG. 13 illustrates one of the many advantages attendant to the present invention. This figure illustrates that more than one column can be secured to a base platform 18. One predicate for this advantage is the design of the clip 10. The dimensions and structural components of the clip 10 of the present invention permit the securing of multiple columns on one base platform 18 as depicted in FIG. 13. The pitch (i.e., the distance between the axis from one column to the axis of a parallel column) is determined by the column's dimensions and not by the clip 10 of the present invention. This pitch distance is minimized using the clip 10 thus allowing for more columns to be secured on, for example, a base platform 18. Preferably, the pitch distance ranges from about 12.5 mm or greater. Essentially, finger access and comfort determine the pitch distance. Hence, the pitch distance will vary from practitioner to practitioner. Therefore, the column-interface 14 of the clip 10, specifically, the grasper 24, is intended to interact with a column's fitting 26 and not the column proper. If the grasper 24 were intended to interact with the column proper, then the preferable pitch distance would not be met, hence, fewer columns could be accommodated on a base platform 18. This would be exemplified by employing a clamp to hold the column to a securing device. This type of clamp would be similar to those used in chemistry laboratories used to secure glass-ware to various securing devices.

Materials suitable for constructing the clip include, but are not limited to, metals like stainless steal, plastic polymers and alike. It is important that these materials be durable and resistant to corrosion. Moreover, it is preferable that the gasper portion be pliable like those embodiments represented by FIGS. 1, 2, 4, 11 and 12. During manufacturing, substances like glass, silica or alike can be added to the material being used for construction of the clip. The additional substance can be added in order to in part memory to the clip for maintaining its original configuration.

What is claimed is:

1. A device for holding a chromatography column, said chromatography column having a cylinder and two ends for receiving fittings, said device comprising:
    a first clip and a second clip, each of said first clip and said second clip having a body having a bar section and a column section, said bar section having bar affixing means for slidably gripping a bar, said bar having a length and a plurality of sides, and at least two of said sides comprising a first column receiving side and a second column receiving side, said bar affixing means having at least one bar alignment surface for being placed in abutting relationship with one of said column receiving sides, and encircling surfaces consisting of fingers constructed and arranged to grasp said support bar or a bar opening in said body, wherein each body can be slid along the length of said bar to accommodate different columns and columns held by additional groups of first clips and second clips,
    said first clip having a column section extending outward from said bar section perpendicular to one of said column receiving sides and having column receiving means constructed and arranged to affix at least one of a chromatography column along its cylinder and a fitting affixed at a first end of a chromatography column; said second clip constructed and arranged to secure said chromatography column at a second end or at one fitting at said second end in parallel alignment with respect to said bar at one end receiving side to allow additional groups of first and second clips to secure multiple columns to said bar on different column receiving sides and lengths of said bar.

2. The device of claim 1 further comprising a bar having a length and a plurality of sides, and at least two of said sides comprising a first column receiving side and a second column receiving side.

3. The device of claim 2 further comprising a stand affixed to said bar for holding said bar with respect to a work surface.

4. The device of claim 1 wherein said column receiving means comprise an opening for receiving a column cylinder or a fitting.

5. The device of claim 1 wherein said column receiving means comprise at least a first finger and a second finger, said first finger and said second finger each having at least one of column and fitting gripping surfaces and said device is a single unitary structure.

6. The device of claim 1 wherein said column receiving means comprise at least a first finger and a second finger, said first finger and said second finger each having at least one of column and fitting gripping surfaces and said first finger and second finger have an open position and a closed position.

7. The device of claim 6 wherein said fingers are compelled to said closed position by springs.

8. The device of claim 5 wherein device has a finger locking means.

9. The device of claim 8 wherein said finger locking means is a finger cap.

10. The device of claim 8 wherein said finger locking means is a wire gate and notch, said wire gate rotatably affixed to said first finger said second finger having a notch for securing said wire gate, said wire gate for assuming an open position to allow said first finger and second finger to receive a column or fitting and assuming a closed position in which said wire gate is received in said notch to secure said column.

11. The device of claim 1 wherein said first clip and said second clip are plastic.

12. A device for holding a chromatography column, said chromatography column having a cylinder and two ends for receiving fittings, said device comprising:

a first clip and a second clip, each of said first clip and said second clip having a body having a bar section and a column section, said bar section having bar affixing means for slidably gripping a bar, said bar having a length and a plurality of sides, and at least two of said sides comprising a first column receiving side and a second column receiving side, said bar affixing means having at least one bar alignment surface for being placed in abutting relationship with one of said column receiving sides, and encircling surfaces consisting of fingers constructed and arranged to grasp said support bar or a bar opening in said body, wherein each body can be slid along the length of said bar to accommodate different columns and columns held by additional groups of first clips and second clips, said first clip having a column section extending outward from said bar section perpendicular to one of said column receiving sides and having column receiving means constructed and arranged to affix at least one of a chromatography column along its cylinder and a fitting affixed at a first end of a chromatography column; said column receiving means selected from the group consisting an opening, and a first finger and second finger, each first finger and second finger having at least one of column and fitting gripping surfaces, said column receiving means for receiving a column cylinder or a fitting, said second clip constructed and arranged to secure said chromatography column at a second end or at one fitting at said second end in parallel alignment with respect to said bar at one end receiving side to allow additional groups of first and second clips to secure multiple columns to said bar on different column receiving sides and lengths of said bar.

13. The device of claim 1 wherein said first clip column section and said second clip column section are constructed and arranged to secure said chromatography column at said fitting affixed at a first end of a chromatography column and said fitting at said second end.

14. The device of claim 1 wherein said device is a single unitary piece.

15. The device of claim 1 wherein said clip column receiving means is constructed and arranged to secure said chromatography column by a snap fit type interaction with said column cylinder or fitting.

* * * * *